US012303421B2

United States Patent
Hoshino

(10) Patent No.: US 12,303,421 B2
(45) Date of Patent: May 20, 2025

(54) LUMBAR PILLOW AND LUMBAR PILLOW SET

(71) Applicant: GAISENN LLC, Gifu (JP)

(72) Inventor: Masashi Hoshino, Gifu (JP)

(73) Assignee: GAISENN LLC, Gifu (JP)

( * ) Notice: Subject to any disclaimer, the term of this patent is extended or adjusted under 35 U.S.C. 154(b) by 359 days.

(21) Appl. No.: 17/909,253

(22) PCT Filed: Mar. 9, 2021

(86) PCT No.: PCT/JP2021/009104
§ 371 (c)(1),
(2) Date: Sep. 2, 2022

(87) PCT Pub. No.: WO2021/187210
PCT Pub. Date: Sep. 23, 2021

(65) Prior Publication Data
US 2023/0090489 A1    Mar. 23, 2023

(30) Foreign Application Priority Data
Mar. 19, 2020 (JP) .................................. 2020-048646

(51) Int. Cl.
*A61F 5/00* (2006.01)
*A47C 7/42* (2006.01)
(Continued)

(52) U.S. Cl.
CPC .............. *A61F 5/028* (2013.01); *A47C 7/425* (2013.01); *A47G 9/10* (2013.01)

(58) Field of Classification Search
CPC ....................................................... A61F 5/028
(Continued)

(56) References Cited

U.S. PATENT DOCUMENTS 4,431,232 A * 2/1984 Hannouche ............ A47C 7/425
297/452.32
5,097,847 A * 3/1992 Mikhail ................. A61G 13/12
128/853
(Continued)

FOREIGN PATENT DOCUMENTS

CH          673771 A5 * 12/1990
CN        206659978 U    11/2017
(Continued)

OTHER PUBLICATIONS

International Application No. PCT/JP2021/009104, International Search Report, Written Opinion, 10 pages, Jun. 1, 2021.

*Primary Examiner* — Kim M Lewis
(74) *Attorney, Agent, or Firm* — Peacock Law P.C.; Justin R. Muehlmeyer

(57) ABSTRACT

A lumbar pillow of height 9 to 11 cm has outer and inner cushioning members, with a hollow space formed in the outer cushioning member. The inner cushioning member has an identical cross-sectional shape as the hollow space. The load X for the user having the lumbar pillow placed under the user's lower back equals a value obtained by multiplying the user's weight by a coefficient 0.59. A preferable range of the amount of displacement against the load is defined. The comfort of the lumbar pillow may be determined on the basis of sensory evaluation including evaluation of the texture during use, and the lumbar pillow can be used for a long period of time. The physical properties may be visualized by providing a plurality of settings to provide a substantially straight load-displacement line, enabling any user to choose a suitable pillow regardless of race, gender, and weight.

19 Claims, 5 Drawing Sheets

(51) Int. Cl.
*A47G 9/10* (2006.01)
*A61F 5/02* (2006.01)

(58) Field of Classification Search
USPC ........................................ 5/630, 633; 602/19
See application file for complete search history.

(56) References Cited

U.S. PATENT DOCUMENTS

| | | | | |
|---|---|---|---|---|
| 5,425,567 | A | * | 6/1995 | Albecker, III ........... A47C 7/46 297/452.29 |
| 5,755,647 | A | * | 5/1998 | Watnik ............. A63B 23/03575 482/121 |
| 5,824,013 | A | * | 10/1998 | Allen ........................ A61F 5/01 606/240 |

FOREIGN PATENT DOCUMENTS

| | | | |
|---|---|---|---|
| CN | 210130671 U | | 3/2020 |
| CN | 2010130671 U | * | 3/2020 |
| JP | H05217580 U | * | 3/1993 |
| JP | 7-17165 U | | 3/1995 |
| JP | 2005-211648 A | | 8/2005 |
| JP | 2013-90889 A | | 5/2013 |
| JP | 2015-43825 A | | 3/2015 |
| JP | 2016-185330 A | | 10/2016 |

* cited by examiner

LUMBAR PILLOW AND LUMBAR PILLOW SET

CROSS-REFERENCE TO RELATED APPLICATIONS

This application is a national stage of International Patent Application No. PCT/JP2021/009104, filed on Mar. 9, 2021; which claims priority to Japanese Patent Application No. 2020-048646, filed on Mar. 19, 2020; the entire contents of each of which is incorporated by reference herein.

TECHNICAL FIELD

The present technology relates to a lumbar pillow and a lumbar pillow set. In particular, the present technology relates to a lumbar pillow usable in the prevention, improvement of symptoms, and treatment of discogenic lower back pain, and a lumbar pillow set combining a lumbar pillow and a knee pillow.

BACKGROUND

When a person walks, the S-shaped curve of his or her spine absorbs the gravitational force acting on his or her body. The lumbar spine is curved inward, but if a person continuously performs actions or maintains a posture in which this curvature is lost, he or she may suffer from lower back pain. Accordingly, maintaining the inward curvature of the lumbar spine can prevent lower back pain. In addition, restoring the inward curvature of the lumbar spine can treat or prevent lower back pain. According to Jiro KOHARA in "Interia Ningen Kogaku" (Gaia Books), the inward curvature of the lumbar spine in the supine position is 2 to 3 cm.

In lower back pain treatment overseas, exercises for restoring the inward curvature of the lumbar spine, known as the McKenzie method, enjoy widespread support. The McKenzie method constitutes exercises in which the body is bent backward, and was developed by New Zealand physical therapist Robin McKenzie around 1956. Specifically, the method involves first lying prone, face turned forward, then planting the hands like when doing a push-up and straightening the elbows to gradually raise the upper body. At this time, the lower back and legs are relaxed. In order to maximize the backward bending of the lower back, the arms are extended as far as possible while exhaling. This pose is held for 5 to 10 seconds to make one set, and several sets are performed in a day. There is also a method that is done while standing up.

Conventionally, in the field of discogenic lower back pain treatment in Japan, many professionals including orthopedic surgeons held the outdated belief that bending the lower back backward exacerbates lower back pain. As a result, treatment in which the lower back is bent backward was not performed until recently. A conventional treatment method is described on page 124 and page 212 of "Yotsu Koshite Naosu" by Yoshiomi YAMAGUCHI (Shufunotomosha, Co., Ltd., 1990).

"3 Byo! Kore Dake Taiso" (3 Seconds! One Little Exercise) by Ko MATSUDAIRA (Makino Shuppan, "Anshin") was published in 2015. Later, in 2019, the television network NHK broadcast the details of the exercise. In the light of this information, experts began to praise the exercise of bending the lower back backward as a revolutionary treatment method. In MATSUDAIRA's "3 Seconds! One Little Exercise," the "one little exercise" of bending the lower back backward is explicitly stated to have been proposed based on McKenzie's theory, and the mechanics behind lower back pain are also described. Further, it is also emphasized that in order to treat lower back pain, it is necessary to restore the inward curvature of the lumbar spine (i.e., to restore it to the original position).

It is now clear that both the McKenzie method and the "one little exercise" of bending the lower back backward are effective in both preventing and treating discogenic lower back pain.

The mechanics of discogenic lower back pain will be described. The intervertebral discs between the vertebral bodies that constitute the spine serve as cushions, and contain a gel-like substance called nucleus pulposus. Normally, the nucleus pulposus is positioned in the center of the intervertebral disc. However, if a person maintains a poor posture or a forward stooped posture for a long period of time, or strains the back by overextension, intervertebral discs in the lumbar portion are compressed, which causes the nucleus pulposus to become displaced (slip) from the center toward the back side. This movement causes lower back pain. If the nucleus pulposus remains in this displaced state without returning to the center, the lower back pain may become chronic. It is therefore important not to ignore displacement of the nucleus pulposus, but to return (restore) it as soon as possible.

Before the publication of MATSUDAIRA's "3 Seconds! One Little Exercise,", the inventor filed Japanese Patent Application No. 2011-246898 for an invention relating to a pillow for restoring the inward curvature of the lumbar spine and a method using the pillow, which was registered as Japanese Patent No. 5626657. The inventor also filed Japanese Design Application No. 2014-023488 for a design of a pillow for restoring the inward curvature of the lumbar spine, which was registered as Japanese Design No. 1535266.

There are many other exercises and osteopathic treatments involving backward bending of the lower back, indicating that the importance of such backward bending is finally being recognized.

SUMMARY OF THE INVENTION

Problems to be Solved by the Invention

The lumbar pillow disclosed in Japanese Patent No. 5626657 (hereinafter referred to as a conventional lumbar pillow) has a semi-hard cushioning material, and thus presses the lumbar spine strongly. Therefore, it is usable for a short period of time, but has a shortcoming in that the lumbar body pressure distribution is concentrated in a small area and therefore the pillow cannot be used for a long period of time.

When people of different physiques and body weights use the conventional lumbar pillow, it is unclear to which degree to set the body pressure distribution area, and how much displacement is optimal against the load. There is therefore a need to identify the physical properties of a lumbar pillow that an unspecified number of people of different physiques and body weights can use. There is also a need to identify a shape of a lumbar pillow that Asians, Westerners, or other people of various physiques can use.

With the conventional lumbar pillow, there were a few people who felt a slight discomfort when the pillow made contact with their skin in the initial stage of lying down on the pillow in the supine position (this discomfort is also referred to as "texture" below), or felt a slight discomfort when receiving the reaction force from the pillow. Measures need to be taken to relieve the discomfort of such users.

When the conventional pillow was used in the supine position, it was unclear whether or not prevention of discogenic lower back pain was possible.

The present technology was made to solve the above problems, and has a purpose of maintaining and restoring the inward curvature of the lumbar spine, and providing a lumbar pillow that is more comfortable to use.

Means for Solving the Problems

In a first implementation, the present technology relates to a lumbar pillow.

The lumbar pillow according to the present technology maintains an inward curvature of a lower back of a user by being in contact with the lower back of the user in a supine position or a sitting position, the lumbar pillow having a height of 9 cm to 11 cm, and includes:
- an outer cushioning member formed of a semi-hard foam; and
- an inner cushioning member formed of a semi-hard foam having a lower hardness than the outer cushioning member,
- wherein a cross-sectional shape of an outer peripheral portion of the outer cushioning member is a partially cylindrical shape provided with a horizontal bottom surface and a top surface composed of a curved surface having three or more different radii of curvature,
- wherein in a central portion of the cross-section, there is formed an approximately dome-shaped hollow space wherein a top surface composed of a curved surface having two different radii of curvature is formed on a vertical side surface at a different height than the horizontal bottom surface,
- the inner cushioning member has an identical cross-sectional shape to that of the hollow space,
- the outer cushioning member and the inner cushioning member have a constant shape in a longitudinal direction, and
- wherein when the lumbar pillow is placed under the lower back of a user lying in the supine position, a load X applied to the lumbar pillow from the user is equal to a value obtained by multiplying a weight W of the user by a coefficient 0.59, and
- in the following Formula (1) that represents a range Y of an amount of displacement of the lumbar pillow against the load X, $$Y(mm) = \{Y_0 + \tan \alpha \times X(kg)\} \pm 8 \quad \text{(Formula 1):}$$

wherein when the load X is 26 kg to 41.5 kg,
$Y_0 = 37$ (constant, unit mm),
$\tan \alpha = Y_1 - Y_0 / X_1 - X_0 = 0.97$ (coefficient), and
load X=an increased load from $X_0$ to any given point (unit kg),
and wherein when the load X is 41.5 kg to 65 kg,
$Y_0 = 52$ (constant, unit mm),
$\tan \alpha = Y_2 - Y_1 / X_2 - X_1 = 0.68$ (constant), and
load X=an increased load from $X_1$ to any given point (unit kg).

The inventor discovered that a preferable height of the lumbar pillow is 9 cm to 11 cm, and that the load applied to the lumbar pillow is equal to a value obtained by multiplying the user's weight by 0.59, and found that this quantifies the load applied to the lumbar pillow and the displacement amount, and allows for the provision of an optimal displacement amount range.

In a second implementation, the present technology further relates to a lumbar pillow set provided with a lumbar pillow and a knee pillow.

The lumbar pillow set according to the present technology includes:
- the lumbar pillow according to the first implementation, as summarized above;
- a knee pillow that has a constant shape in the longitudinal direction and a cross-section in the shape of a scalene triangle with a peak cut off, and is formed of a cushioning member of a semi-hard foam; and
- a length-adjustable belt for connecting the lumbar pillow and the knee pillow.

The lumbar pillow and the lumbar pillow set according to the present technology were made on the basis of the same theory of lower back pain treatment and prevention as the McKenzie method and the "one little exercise," and can be expected to be effective both in prevention and treatment of discogenic lower back pain.

Using the lumbar pillow or the lumbar pillow set composed of the lumbar pillow and the knee pillow according to the present technology erases the doubts patients suffering from lower back pain may have regarding "whether or not it can be prevented." As a result, this contributes greatly to reducing the number of patients suffering from lower back pain. In other words, by using this pillow in the supine position every day, the nucleus pulposus will not move much, and even if it does move, it will recover the same night, which reduces the occurrences of lower back pain.

Effects of the Invention

By a combination of an inner cushioning member and an outer cushioning member having different degrees of hardness, and the synergistic effect of the shape of the top surface composed of a curved surface, the lumbar pillow according to the present technology does not concentrate the body pressure distribution of the lower back. In addition, the displacement amount of the lumbar pillow is quantified and increases in proportion to the load on the lumbar pillow, and therefore, within the range thereof, discomfort at the contact portion is low, and the texture is pleasant.

The lumbar pillow according to the present technology quantifies the relationship between the load from the user and the user's weight, and provides an optimal displacement amount range, thereby resolving a shortcoming of conventional lumbar pillows in that "the lumbar body pressure distribution is concentrated in a small area and therefore the pillow cannot be used for a long period of time." In other words, by optimizing the displacement amount when the user applies a load to the lumbar pillow, concentration of the body pressure distribution of the lower back is avoided, and the body pressure distribution becomes optimal. Therefore, the pillow can be used for a long period of time.

Further, Asians, Westerners, men, women, and overweight people were sorted by weight and body type to quantifiably visualize the optimal body pressure distribution and displacement amount. As a result, it is easier for a user to select a pillow that fits the user, allowing the user to use the lumbar pillow according to the present technology comfortably.

The lumbar pillow set according to the present technology can be used by placing the lumbar pillow in contact with the lumbar spine portion and placing the knee pillow in contact with the knees. Comparing use of the lumbar pillow set and the use of only the lumbar pillow, the load applied to the pillow can be "eased" by moving to the gluteal region, and discomfort can be reduced by increasing the number of supporting points. The lumbar pillow set thus exhibits an effect of reducing body pressure and relieving discomfort during use.

DETAILED DESCRIPTION

First, an operation of a lumbar pillow and a lumbar pillow set according to the present technology is described, and then, one embodiment of the lumbar pillow and the lumbar pillow set is described with reference to the drawings.

Operation of the Lumbar Pillow and the Lumbar Pillow Set

Lower back pain is caused by the nucleus pulposus becoming displaced from the center toward the back side when the intervertebral discs are compressed due to a person maintaining a poor posture for a long period of time, or straining the back by overextension. One way to prevent lower back pain is to not ignore displacement of the nucleus pulposus and returning it as soon as possible, or to avoid displacement. The lumbar pillow according to the present technology is able to maintain or restore a user's inward curvature of the lumbar spine by making contact with the user's lumbar spine when supine or seated.

Shape of the Lumbar Pillow

Figure 1:
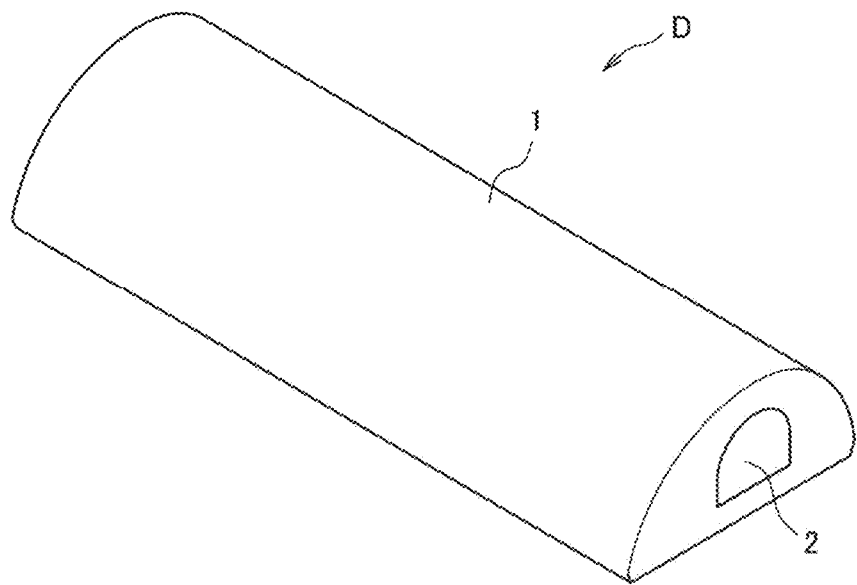
FIG. 1 is a perspective view of a lumbar pillow according to the present technology.
Figure 2:
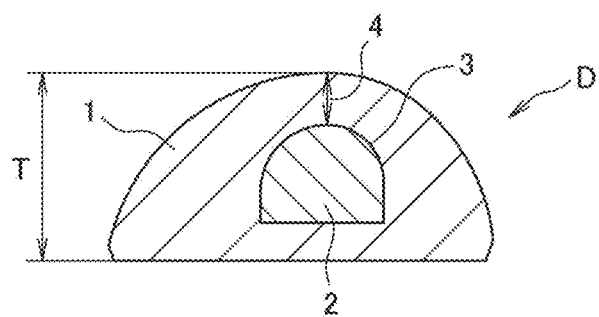
FIG. 2 is a cross-sectional view of the lumbar pillow according to the present technology.

FIG. 1 is a perspective view of the lumbar pillow D according to the present technology, and FIG. 2 is a cross-sectional view of the lumbar pillow D according to the present technology. The lumbar pillow D according to the present technology has a total height T of 9 cm to 11 cm. The lumbar pillow D is provided with an outer cushioning member 1 and an inner cushioning member 2 formed of a semi-hard foam with a lower hardness than that of the outer cushioning member 1. The cross-sectional shape of an outer peripheral portion of the outer cushioning member 1 is a partially cylindrical shape provided with a horizontal bottom surface and a top surface composed of a curved surface having three or more different radii of curvature. In a central portion of the cross-section, there is formed an approximately dome-shaped hollow space 3, wherein a top surface composed of a curved surface having two different radii of curvature is formed on a vertical side surface at a different height than the horizontal bottom surface, and the inner cushioning member 2 having the same shape as the hollow space 3 is contained therein. The outer cushioning member 1 and the inner cushioning member 2 have a constant shape in the longitudinal direction.

The shape of the top surface of the outer cushioning member 1 is formed in accordance with the shape of the lumbar spine. Thus, the radius of curvature of the surface that is to make contact with the upper back of a user is greater than that of the surface that is to make contact with the lower back of the user, and forms a gently-curving surface. Hereinafter, the distance from the top of the hollow space 3 in the outer cushioning member 1 to the peak of the top surface is also referred to as an arch peak thickness 4.

The semi-hard foam constituting the outer cushioning member 1 and the inner cushioning member 2 is a foamed plastic material, wherein an elastic modulus E of a resin is 700 to 7000 kgf/cm$^2$, or a reduction in thickness after 50% compression and subsequent release is 2 to 10%. The most common semi-hard foam is urethane foam.

In other words, the lumbar pillow D according to the present technology has an outer cushioning member 1 made of a semi-hard foam. The cross-sectional shape of the outer cushioning member 1 is an asymmetrical arch near the top, and has a partially cylindrical hollow space 3 in its center. The outer cushioning member 1 extends linearly in the longitudinal direction. An inner cushioning member 2 made of a semi-hard foam with a slightly lower hardness is seamlessly inserted into the hollow space 3 of the outer cushioning member 1. Optionally, a removable cover not illustrated here may be used to cover the lumbar pillow.

According to the results of an amount of displacement comparison test between a case wherein the inner cushioning member 2 of the same shape as the hollow space 3 is inserted seamlessly and a case wherein gaps are present between the hollow space 3 and the inner cushioning member 2, there is a greater difference than the gaps account for. In other words, a case wherein gaps are present exhibits a greater amount of displacement than the gaps. Therefore, in order to eliminate unnecessary displacement, the inner cushioning member 2 may be inserted seamlessly into the hollow space 3.

Shape of the Lumbar Pillow Set

Figure 3:
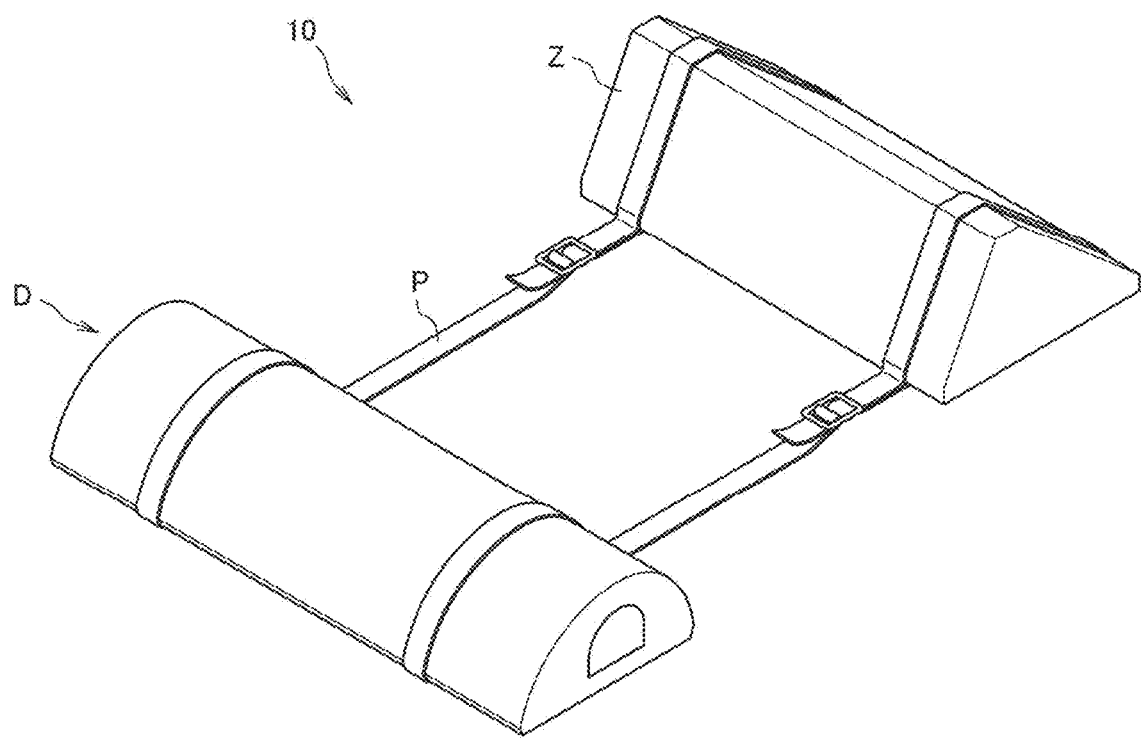
FIG. 3 is a perspective view of a lumbar pillow set according to the present technology.

FIG. 3 is a perspective view of a lumbar pillow set 10. In addition to the lumbar pillow D, the lumbar pillow set 10 is provided with a knee pillow Z and a belt P. The knee pillow Z has a constant shape in the longitudinal direction, has a cross-section in the shape of a scalene triangle with the peak cut off, and is formed of a cushioning member of a semi-hard foam. The belt P has an adjustable length and connects the lumbar pillow D and the knee pillow Z to each other.

The knee pillow Z is a member for relieving the user's discomfort, and may optionally be covered with a removable cover. Two length-adjustable belts P may be used in parallel to connect the lumbar pillow D and the knee pillow Z to each other. The belts P are arranged in parallel at both ends of the lumbar pillow D, and after adjusting the distance to the knee pillow Z, may fasten the two pillows to each other. The user may place the lumbar pillow D under his or her lumbar spine and the knee pillow Z under his or her knees at a desired distance and position.

There is no need to limit the shape and material of the belt P, and any connective component may be used.

By having the shape of the knee pillow Z be a scalene triangle with the peak cut off, people of different knee heights and leg lengths may change which side of the pillow to use, thereby adjusting the position of their legs and the texture. Further, by having the peak of the knee pillow Z be cut off, concentration of the below-knee load (foot weight) can be alleviated.

Optimizing the Body Pressure Distribution of the Lumbar Pillow

Figure 4:
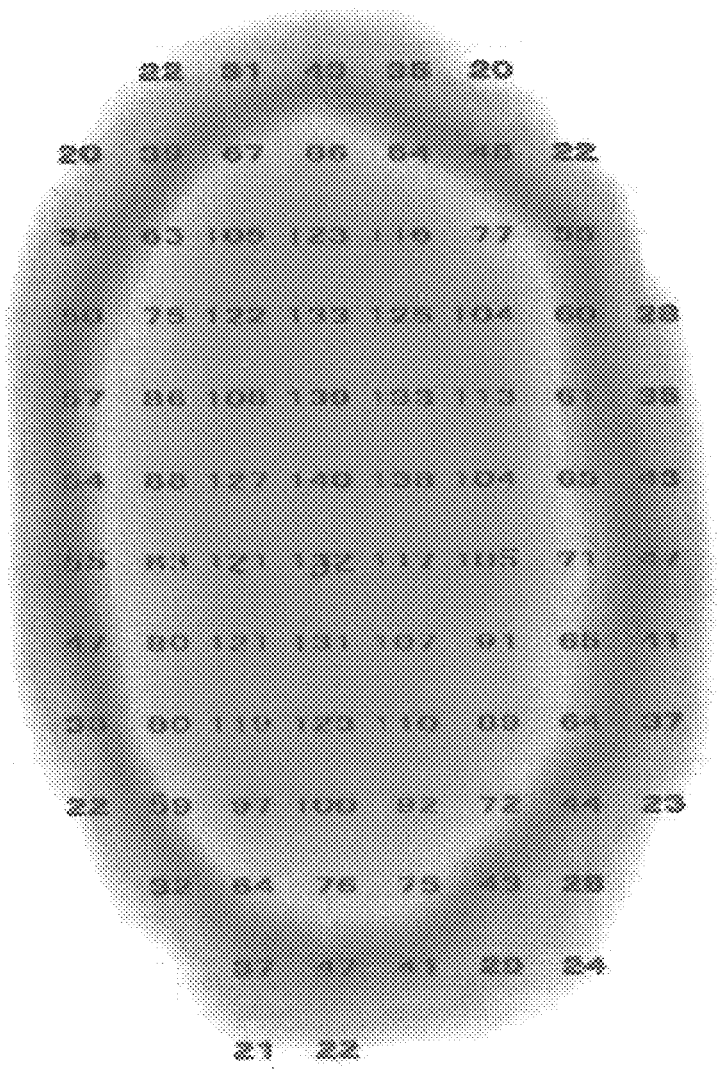
FIG. 4 illustrates an example of a body pressure distribution test result for the lumbar pillow according to the present technology.
Figure 5:
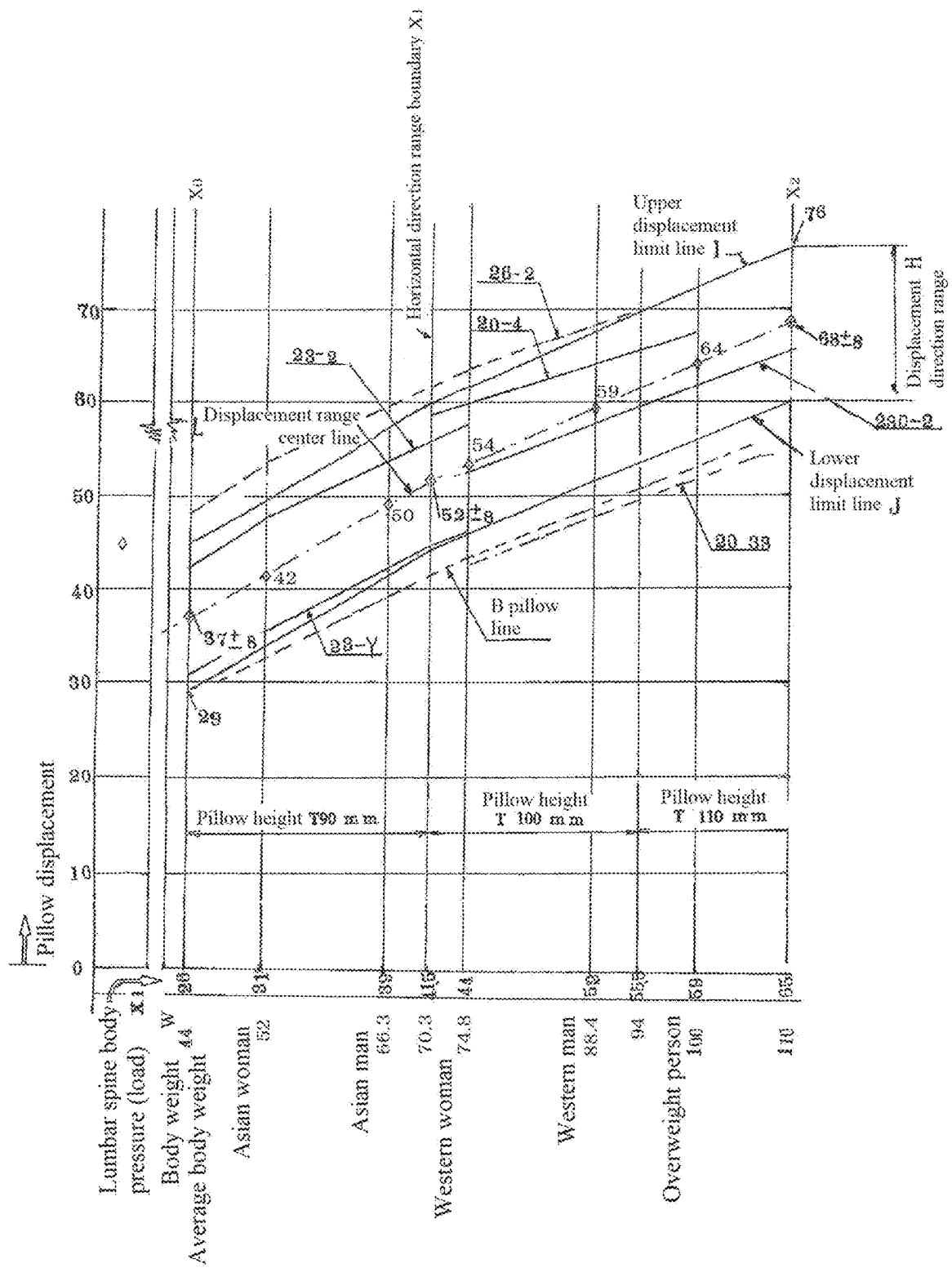
FIG. 5 is a graph indicating a range of displacement against the load of the lumbar pillow according to the present technology.
Figure 6:
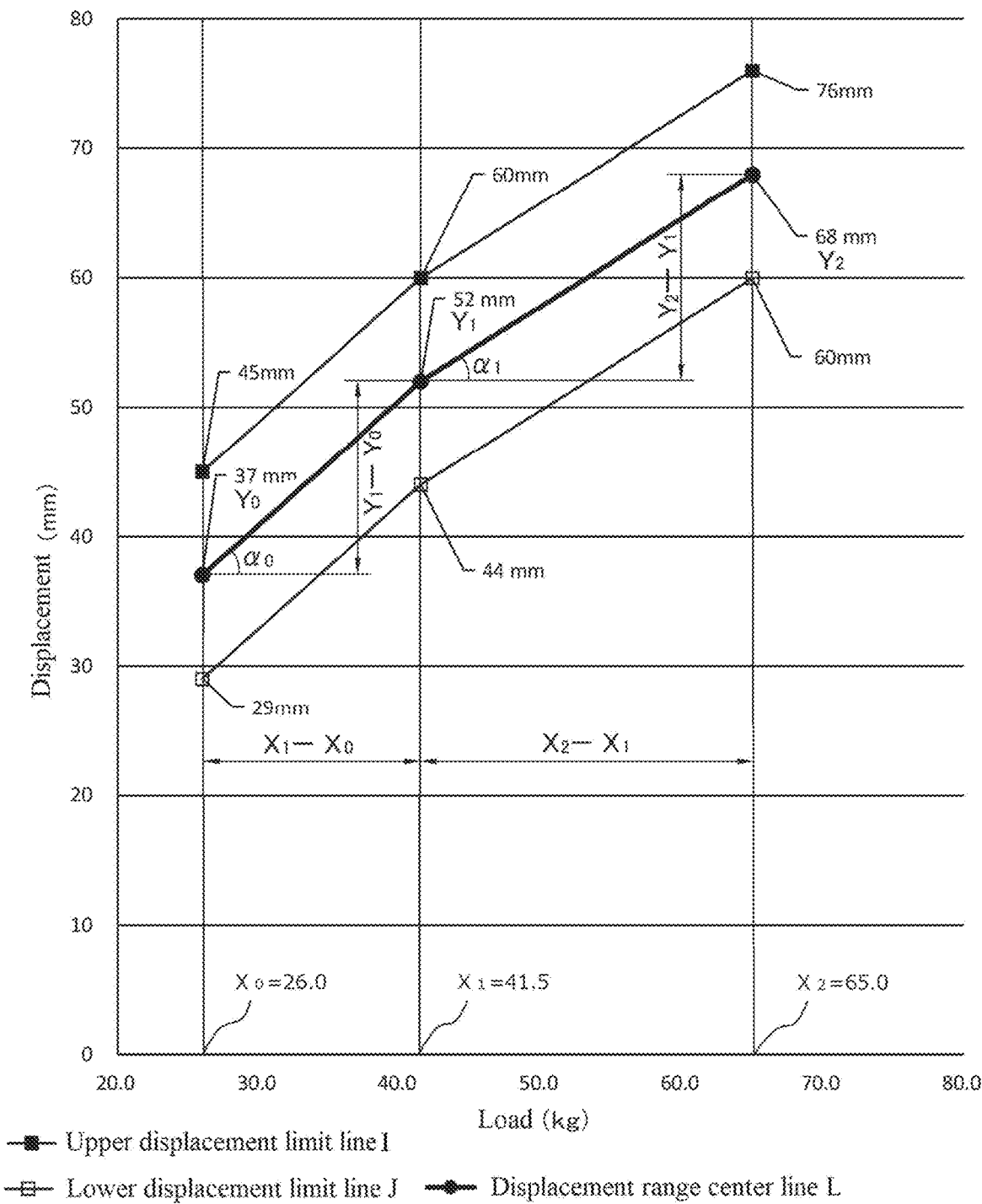
FIG. 6 is a graph indicating all ranges of displacement against the load of the lumbar pillow according to the present technology.

With reference to FIGS. 4 to 6, optimization of the user's body pressure distribution when the lower back makes contact with the lumbar pillow when the user is in the supine position will be described. The body pressure distribution is concentrated in a smaller area with a harder lumbar pillow D, and is distributed over a larger area with a softer lumbar pillow D. In the lumbar pillow D according to the present technology, the area is not used as an index, but the hardness of the lumbar pillow D is adjusted such that the relationship between the load applied to the lumbar pillow D and the amount of displacement of the lumbar pillow is optimized, thereby optimizing the body pressure distribution on the lumbar pillow D.

The dimensions and the physical properties of the lumbar pillow D for a preferable body pressure distribution satisfy the following relationships.

First, the total height T of the lumbar pillow D is set to be within the range of 9 to 11 cm. The lighter the user, the lower the lumbar pillow D to be applied. Conversely, when the user is heavy, a taller lumbar pillow D is applied.

Second, by optimizing the shape and material of the outer cushioning member 1 of the lumbar pillow D according to the present technology, a load X applied to the lumbar pillow D is equal to a value obtained by multiplying the user's weight W by a coefficient 0.59. The relationship between the user's weight and the load applied to the lumbar pillow was identified by the results of usage tests by users of different weights using a B pillow (pillow with physical properties indicated by the B pillow dashed line in FIG. 5) and a test piece of the lumbar pillow D according to the present technology, and the results converged on the coefficient 0.59. As an example, FIG. 4 illustrates the body pressure of a user weighing 66.3 kg lying in the supine position with the B pillow under the lumbar spine, as measured by an instrument for measuring body pressure distribution. This resulted in the load X being equal to 39 kg, and the body pressure distribution area being 426 cm². These results approximately converged on a ratio of the user's weight to the body pressure of the lumbar spine portion being equal to 1.0:0.59.

Third, the range of the amount of displacement of the lumbar pillow according to the present technology when a user lies in the supine position with the lumbar pillow under his or her lower back can be represented by the following Formula (1).

Amount of displacement range $Y(mm)=\{Y_0+\tan \alpha \times X (kg)\} \pm 8$      (Formula 1):

wherein, when the load X is 26 kg to 41.5 kg, $Y_0=37$ (constant, unit mm), $\tan \alpha = Y_1-Y_0/X_1-X_0=0.97$ (coefficient), and load X=an increased load from $X_0$ to any given point (unit kg), and wherein, when the load X is 41.5 kg to 65 kg, $Y_0=52$ (constant, unit mm), $\tan \alpha = Y_2-Y_1/X_2-X_1=0.68$ (constant), and load X=an increased load from $X_1$ to any given point (unit kg).

A preferable height of the lumbar pillow D could be determined by taking into account the relationship between body weight and the load X applied to the lumbar pillow D, in addition to the comfort during use in the supine position and maintaining the inward curvature of the lumbar spine. For a user weighing 44 kg to 70.3 kg, a lumbar pillow with a height of 9 cm may be preferable. For a user weighing 70.3 kg to 94 kg, a lumbar pillow with a height of 10 cm may be preferable. For a user weighing 94 kg or more, a lumbar pillow with a height of 11 cm may be preferable.

Even when a lumbar pillow with a preferable height is used, if the amount of displacement of the lumbar pillow D against the user's weight is too small, the user will feel discomfort and will not be able to use the lumbar pillow for a long period of time. Conversely, if the amount of displacement of the lumbar pillow D against the user's weight is too great, the lumbar pillow D will be compressed to such a degree that the inward curvature of the lumbar spine cannot be maintained. Similar to the body pressure distribution test, users of different weights used the lumbar pillow D, and the preferred relationship between the load and the amount of displacement range of the lumbar pillow is illustrated in the graph of the range of preferred displacement against the load in FIG. 6.

The relationship between the load and the amount of displacement in FIG. 6 satisfies the relationship in Formula 1. As a result of the various tests indicated in the examples below, when using a lumbar pillow with a smaller amount of displacement than the lower amount of displacement limit line J in FIG. 6, i.e., a hard lumbar pillow, users tended to feel discomfort. On the other hand, when using a lumbar pillow with a greater amount of displacement than the upper amount of displacement limit line I in FIG. 6, i.e., a soft lumbar pillow, there was a risk that the inward curvature of the lumbar spine of the user could not be maintained, and no effect could be obtained. Accordingly, a preferable lumbar pillow may have physical properties within the range between the lower amount of displacement limit line J and the upper amount of displacement limit line I against the load, as illustrated in FIG. 6.

EXAMPLES

Below, examples of users of the lumbar pillow and the lumbar pillow set according to the present technology are described in more specific detail with reference to FIG. 5.

Displacement of the lumbar pillow D is approximately proportional to the load applied to the lumbar pillow D. This operation is a combined effect of the strength of the outer cushioning member 1, the strength of the inner cushioning member 2, and the arch peak thickness 4. By the displacement of the lumbar pillow D being approximately proportional to the load applied to the lumbar pillow D is meant that the displacement against the load changes linearly (in the relationship of a linear function). Hereinafter, the graph indicating the value of displacement against the load is also referred to as a "load-displacement line". By employing the portion wherein this load-displacement line is substantially straight, a preferable body pressure distribution is achieved.

The measurement of the arch peak thickness 4 accordingly to the present technology may be 20 mm to 25 mm. If the arch peak thickness 4 exceeds 25 mm, the user will feel the hardness when making contact with the pillow, resulting in a lower sensory evaluation score due to poor comfort and texture, etc. However, other than the arch peak thickness 4, the physical properties and the shape of the outer cushioning member 1 and the inner cushioning member 2 may also be considered important for the sensory evaluation.

Investigating the Problem of Texture Discomfort

FIG. 5 also describes providing a preferred range of displacement of the pillow against the load (displacement direction range H) for users of different race, gender, and weight. The lines indicating the ranges are the upper amount of displacement limit line I, the displacement range center line L, and the lower amount of displacement limit line J. It was considered which of these three lines to investigate in order to perform a survey regarding sensory impressions such as texture. It was found that investigating displacement lines approaching the lower amount of displacement limit line J, which is the boundary of the preferred displacement range, would facilitate the survey and statistical observation. The lumbar pillow that has such an approaching displacement line is a test pillow B described below.

With conventional lumbar pillows, a number of users reported discomfort when receiving the reaction force of the pillow, and alleviating this was considered important. Thus, a test pillow B (made by a conventional method and having a height T of 9 cm and an arch peak thickness 4 of 2 cm) having a displacement of 39 mm against the weight of an average Asian man was made, and a survey using a pain scale described below was carried out. As a result, multiple replies reported feeling no pain, and thus the physical properties were near those of the lower amount of displacement limit line J. Importance was thus placed on the lower amount of displacement limit line J where evaluation was possible, and the set order was J, I, L.

Survey Results and Evaluation of Pillow B for Setting the Lower Amount of Displacement Limit Line J The test pillow B was evaluated as having physical properties near those of the lower amount of displacement limit line J, and a large number of test subjects (49 Japanese people) were further monitored. The survey was carried out with 49 Japanese test subjects, and did not distinguish between people with lower back pain and those without, or between genders. The scale was separated into Classes 1 through 4, where Class 1 was Painful, Class 2 was Slightly painful, Class 3 was Tolerable, and Class 4 was Not painful. After a period of 40 days of use, the results were as follows: Class 1: 0 people, Class 2: 4 people, Class 3: 9 people, Class 4: 33 people, No Response: 3 people.

According to a statistical observation, 8% reported feeling pain and 18% reported feeling slight pain, and because many of them were women, it is plausible that their skin sensitivity is expressed. However, in this survey only the results were used in the evaluation, and thus the test pillow B displacement is positioned at the B pillow line in FIG. 5, and was evaluated as being slightly below the lower amount of displacement limit line J.

FIG. 5 indicates a preferred range of displacement of the pillow against the load, and the displacement of the pillow against the load increases or decreases approximately proportionally to the load. FIG. 5 is a graph that visualizes the physical properties, enabling any user to choose a suitable pillow regardless of race, gender, and weight.

Ratio of Weight to Load Applied to Lumbar Pillow

The ratio of weight (kg) to the body pressure of the lumbar portion (kg) applied to the lumbar pillow D is 1:0.59. This body pressure of the lumbar portion applied to the lumbar pillow D is also referred to as "load X" below. The numerical values indicated at the upper part of the horizontal axis in FIG. 5 indicate the body pressure of the lumbar portion applied to the lumbar pillow D as the "load".

Determining the Type of Pillow for Each Weight

The weight of a patient with lower back pain is estimated to be about 44 kg to 110 kg. The lower limit value of 44 kg corresponds to the average weight of 12-year-old children in the national health and nourishment survey of Japan (2016) published by the government, and any users below that weight are estimated to be few. Meanwhile, the upper limit value of 110 kg is a value equal to the average weight of Westerners with a 35% increase, and users above this weight are estimated to be few. The load X of the lumbar portion corresponding to this weight range, considering the relationship wherein the load X is equal to a value obtained by multiplying the user's weight W by a coefficient 0.59, is on average about 26 to 65 kg. The displacement Y of the lumbar pillow D corresponding to this value, considering Formula (1), is on average 3.7 cm to 6.8 cm. In order to achieve the operational effect of the displacement of the lumbar pillow D increasing or decreasing proportionally to the load X, the average body pressure of the lumbar portion of 26 kg to 65 kg was divided into three, and a total height T of the lumbar pillow for each division was determined. In the range of a load of 15 kg to 23.5 kg, a linear load-displacement relationship is achieved. Based on this, the load applied to the lumbar pillow D (i.e., the body pressure of the lumbar portion) was divided into three categories: a pillow for Asians, a pillow for Westerners, and a pillow for overweight people.

Average Weight of Women and Men Relating to the Pillow for Asians

Because there is little difference in weight between Asian people and Japanese people, estimated values from data for Japanese people were used for Asian people as well. Based on the 2010 edition of the physical fitness and exercise capacity survey published by the Ministry of Education, Culture, Sports, Science and Technology and the Agency for Cultural Affairs, a simple average for men and women was calculated, excluding people below the age of 20 and people aged 90 or above, and this value was set as the average weight of women and men for the pillow for Asians.

(Average weight of women: 52.0 kg, average weight of men: 66.3 kg.)

Average Weight of Women and Men Relating to the Pillow for Westerners

Because there is little difference in weight between Westerners and Americans, estimated values from data for Americans were used for Westerners as well. Based on an Internet search for "average height and weight of Americans by age" made on Aug. 7, 2017, a simple average for men and women was calculated, excluding people below the age of 20 and people aged 90 or above, and this value was set as the average weight of women and men for the pillow for Westerners.

(Average weight of women: 74.8 kg, average weight of men: 88.4 kg.)

The weight for overweight people was specifically indicated as 100 kg and 110 kg.

In the load direction (horizontal axis direction of the graph) of these ranges, there is a place where the displacement lines of the lumbar pillows bend, and this boundary is near 41.5 kg, which is approximately the middle point of Asians and Westerners, and therefore this boundary was set as the boundary line X1 in the horizontal direction range.

Setting a Suitable Displacement Range of the Lumbar Pillow Against the Load

In order to set a suitable lower amount of displacement limit line J and upper amount of displacement limit line I, 12 pillows D for monitoring were made by a urethane raw material injection method that is the manufacturing method employed, and these were measured using an instrument for measuring load-displacement. By way of example, the D pillow has a bottom surface width (length corresponding to the body height direction of the user) of 18.6 cm, a pillow height T of 9.0 cm, and an arch peak thickness of 2 cm to 2.3 cm, and weighs 850 g to 1050 g. This pillow was made for monitoring purposes and is not intended to limit the scope of claims. Then, based on the measured values of the pillow D, the B pillow measured values, and the evaluation thereof, (1) the lower amount of displacement limit line J, (2) the upper amount of displacement limit lint I, and (3) the displacement range center line L were set in this order.

Setting of the Lower Amount of Displacement Limit Line J

As mentioned regarding the survey results and evaluation of the B pillow, the load-displacement line of the B pillow was evaluated as being slightly below the lower amount of displacement limit line J. Therefore, test pillow 20-33 is outside the displacement direction range, and test pillow 23—Y is within the displacement direction range, and with a margin of ±8 mm for the displacement direction range, the lower amount of displacement limit line J was set as indicated in FIG. 5. However, the 8% who reported feeling pain and the 18% who reported feeling slight pain in the statistical observation are thought to have decreased, but the problem has not been resolved. It was determined that use of the lumbar pillow set described below and reducing the use time period would be a sufficient means of resolution.

Setting of the Upper Amount of Displacement Limit Line I

The upper amount of displacement limit line I is determined with consideration to the curvature of the lumbar portion in the supine position. According to "Interia Ningen Kogaku" by Jiro KOHARA, the curvature is 2 cm to 3 cm when in the supine position, and therefore, the maximum displacement of the pillow is within lumbar pillow height T-3 cm, and the upper amount of displacement limit line I was set as a line connecting the maximum displacement of the pillow at $X_0$, $X_1$, and $X_2$. To determine whether or not this upper amount of displacement limit line I would enable providing a suitable pillow, the measured values of the load-displacement line of the D-pillows were respectively analyzed, whereupon it was found that the test pillows 23-2 and 20-4 were within the displacement direction range, and the test pillow 26-2 exceeded the upper amount of displacement limit line I. Upon comprehensive evaluation, the setting was determined to be suitable.

Determining the Displacement Range Center Line L

The test pillow 23D-2 has the load-displacement line approximately in the center, and is evaluated as a preferred pillow. There is approximately 16 mm between the lower amount of displacement limit line J and the upper amount of displacement limit line I, and therefore, the displacement direction range H is set to 16 mm, and the center line thereof is set as the displacement range center line L.

Lumbar Pillow Height for Weights of 110 kg or More

The pillow height T in the examples was set to 9 cm for Asians, 10 cm for Westerners, and 110 cm for overweight people, but the height is not so limited. Even for a person weighing 110 kg or more, the pillow height T may be changed to be higher, the displacement amount upper limit line I and the displacement amount lower limit line J in FIG. 5 may each be extended, and the displacement direction range H may be set. In other words, even for a person weighing 110 kg or more, a pillow having a suitable body pressure distribution may be achieved by the displacement direction range H setting.

Based on the above results, the suitable physical properties of the pillows for the respective users are as follows.

For a user weighing 52 kg, which is the average weight of an Asian woman, the load on the pillow is 31 kg, and the suitable displacement range is 42±8 mm.

For a user weighing 66.3 kg, which is the average weight of an Asian man, the load on the pillow is 39 kg, and the suitable displacement range is 50±8 mm.

For a user weighing 74.8 kg, which is the average weight of a Western woman, the load on the pillow is 44 kg, and the suitable displacement range is 54±8 mm.

For a user weighing 88.4 kg, which is the average weight of a Western man, the load on the pillow is 52 kg, and the suitable displacement range is 59±8 mm.

For a user weighing 100 kg, which is classified as overweight, the load on the pillow is 59 kg, and the suitable displacement range is 64±8 mm.

Effect of the Lumbar Pillow Set

The lumbar pillow set was invented in order to improve the texture feel when using the pillow in the supine position, as reported in the survey regarding the B pillow, which is a single lumbar pillow D. In the survey, 4 people reported slight pain, and 9 people reported tolerable pain.

For the purpose of relieving discomfort, the lumbar pillow set 10 was made, wherein the knee pillow Z is connected via the belts P. The lumbar pillow set 10 contributes to curving the lumbar spine portion, while reducing and distributing body pressure, and further relieving discomfort. Upon once again monitoring those participants who felt pain when using only the lumbar pillow D, favorable responses were received, reporting that the discomfort had been improved.

DESCRIPTION OF THE REFERENCE NUMERALS

D Lumbar pillow
Z Knee pillow
P Belt
1 Outer cushioning member
2 Inner cushioning member
3 Hollow space
4 Arch peak thickness
T Height of lumbar pillow
10 Lumbar pillow set

The invention claimed is:

1. A lumbar pillow comprising:
   an outer cushioning member formed of a semi-hard foam, and including, in a cross-section:
      a central portion;
      an outer peripheral portion including:
         a horizontal bottom surface; and
         a top surface,
            the bottom surface and the top surface defining a partially cylindrical shape in the cross-section; and
      an approximately dome-shaped hollow space formed in at least a part of the central portion; and
   an inner cushioning member formed of a semi-hard foam and disposed within the hollow space; and
   wherein when the lumbar pillow is placed under the lower back of a user lying in the supine position, a load X [kg] applied to the lumbar pillow from the user is equal to a value obtained by multiplying a weight W of the user by a coefficient 0.59.

2. The lumbar pillow of claim 1, wherein a hardness of the inner cushioning member is lower than a hardness of the outer cushioning member.

3. The lumbar pillow of claim 1, wherein the top surface is composed of a curved surface.

4. The lumbar pillow of claim 3, wherein the curved surface has three or more different radii of curvature.

5. The lumbar pillow of claim 1, wherein the hollow space includes, in a cross-section thereof, a curved top surface.

6. The lumbar pillow of claim 5, wherein the curved top surface of the hollow space has two different radii of curvature.

7. The lumbar pillow of claim 5, wherein the hollow space further includes, in the cross-section thereof, at least one vertical side surface continuous with at least one end of the curved top surface of the hollow space.

8. The lumbar pillow of claim 7, wherein the hollow space further includes, in the cross-section thereof, a horizontal bottom surface continuous with at least the at least one vertical side surface and the at least one end of the curved top surface of the hollow space.

9. The lumbar pillow of claim 8, wherein the at least one vertical side surface has a different height than a height of the horizontal bottom surface.

10. The lumbar pillow of claim 8, wherein the at least one vertical side surface of the hollow space comprises first and second vertical side surfaces on opposite sides of the hollow space, the first and second vertical side surfaces each having a different height than a height of the horizontal bottom surface.

11. The lumbar pillow of claim 7, wherein the hollow space further includes, in the cross-section thereof, two opposing vertical side surfaces respectively continuous with two opposing ends of the curved top surface of the hollow space.

12. The lumbar pillow of claim 11, wherein the hollow space further includes, in the cross-section thereof, a horizontal bottom surface continuous with the two opposing vertical side surfaces and the two opposing ends of the curved top surface of the hollow space.

13. The lumbar pillow of claim 1, wherein a cross-sectional shape of the inner cushioning member and a cross-sectional shape of the hollow space are identical.

14. The lumbar pillow of claim 1, wherein the outer cushioning member and the inner cushioning member have a constant shape in a longitudinal direction.

15. The lumbar pillow of claim 1, wherein a range (Y) of an amount of displacement of the lumbar pillow against the load X is defined as:

$Y[\text{mm}] = \{Y_0 + \tan \alpha \times X\} \pm 8$

16. The lumbar pillow of claim 15, wherein when the load X is 26 kg to 41.5 kg, $Y_0=37$ (constant, unit mm), $\tan \alpha = Y_1 - Y_0/X_1 - X_0 = 0.97$ (coefficient), and load X=an increased load from $X_0$ to any given point (unit kg).

17. The lumbar pillow of claim 15, wherein when the load X is 41.5 kg to 65 kg, $Y_0=52$ (constant, unit mm), $\tan \alpha = Y_2 - Y_1/X_2 - X_1 = 0.68$ (constant), and load X=an increased load from $X_1$ to any given point (unit kg).

18. The lumber pillow of claim 1, wherein the lumbar pillow has a height of 9 cm to 11 cm.

19. A lumbar pillow set comprising:
a lumber pillow including:
an outer cushioning member formed of a semi-hard foam, and including, in a cross-section:
a central portion;
an outer peripheral portion including:
a horizontal bottom surface; and
a top surface,
the bottom surface and the top surface defining a partially cylindrical shape in the cross-section; and
an approximately dome-shaped hollow space formed in at least a part of the central portion; and
an inner cushioning member formed of a semi-hard foam and disposed within the hollow space;
a knee pillow formed of a semi-hard foam, wherein in the longitudinal direction, the knee pillow has a scalene triangle cross-sectional shape with a cut off shape; and
at least one length-adjustable belt for connecting the lumbar pillow and the knee pillow and
wherein when the lumbar pillow is placed under the lower back of a user lying in the supine position, a load X [kg] applied to the lumbar pillow from the user is equal to a value obtained by multiplying a weight W of the user by a coefficient 0.59.

* * * * *